US008646458B2

(12) United States Patent
Bernard

(10) Patent No.: US 8,646,458 B2
(45) Date of Patent: Feb. 11, 2014

(54) EASY-APPLICATION MEATAL PLUG

(75) Inventor: Pascal Bernard, Nieul sur Mer (FR)

(73) Assignee: France Chirirugie Instrumentation, Paris (FR)

( * ) Notice: Subject to any disclaimer, the term of this patent is extended or adjusted under 35 U.S.C. 154(b) by 499 days.

(21) Appl. No.: 12/311,028

(22) PCT Filed: Oct. 8, 2007

(86) PCT No.: PCT/FR2007/001637
§ 371 (c)(1),
(2), (4) Date: Mar. 17, 2009

(87) PCT Pub. No.: WO2008/043905
PCT Pub. Date: Apr. 17, 2008

(65) Prior Publication Data
US 2010/0057024 A1 Mar. 4, 2010

(30) Foreign Application Priority Data
Oct. 9, 2006 (FR) ...................... 06 08829

(51) Int. Cl.
*A61B 17/00* (2006.01)
(52) U.S. Cl.
USPC ........................................ 128/887
(58) Field of Classification Search
USPC ................. 128/887, 846, 857, 831, 864–868; 604/299, 294, 8–9, 515; 623/4.1; 606/199
See application file for complete search history.

(56) References Cited

U.S. PATENT DOCUMENTS

| 5,163,959 | A | | 11/1992 | Herrick | 623/11 |
| 5,283,063 | A | * | 2/1994 | Freeman | 424/427 |
| 5,417,651 | A | * | 5/1995 | Guena et al. | 604/8 |
| 5,423,777 | A | * | 6/1995 | Tajiri et al. | 604/294 |
| 5,723,005 | A | * | 3/1998 | Herrick | 623/4.1 |
| 6,234,175 | B1 | * | 5/2001 | Zhou et al. | 128/887 |
| 7,785,285 | B2 | * | 8/2010 | Kurihashi | 604/9 |
| 2005/0197614 | A1 | * | 9/2005 | Pritchard et al. | 604/8 |
| 2006/0074370 | A1 | * | 4/2006 | Zhou | 604/8 |
| 2006/0106352 | A1 | * | 5/2006 | Kurihashi | 604/301 |

FOREIGN PATENT DOCUMENTS

| JP | 2005000628 | | 1/2005 | A61F 2/14 |
| JP | 2005000628 A | * | 1/2005 | |
| WO | WO 03/057101 A1 | | 7/2003 | A61F 9/007 |

* cited by examiner

*Primary Examiner* — Patricia Bianco
*Assistant Examiner* — Tarla Patel
(74) *Attorney, Agent, or Firm* — Renner, Kenner, Greive, Bobak, Taylor & Weber

(57) ABSTRACT

A meatal plug, comprising a stem and a bulb arranged at one end of the stem, the bulb protruding laterally over said stem, a hole being formed in the plug, and the hole opening at the end of the stem opposite the bulb and said hole extending at least into the bulb, characterized in that the ratio of the height dimension of the stem, measured along its longitudinal axis to the length dimension along this same bulb axis is greater than 1, preferably greater than 2.5, the ratio of the width dimension of the bulb to its length, i.e. measured in a direction perpendicular to the stem axis, is greater than 1, preferably greater than 2.5.

20 Claims, 2 Drawing Sheets

EASY-APPLICATION MEATAL PLUG

TECHNICAL FIELD

The present invention relates to a metal plug intended to plug a metal opening of a tear duct of a human eye. The present invention also relates to a device for positioning a plug of this kind. Lastly, the present invention also relates to a method for plugging a metal opening of a tear duct of a human eye.

BACKGROUND OF THE INVENTION

Metal plugs known today consist of a body comprising a stem and a bulb arranged at one end of the stem and projecting laterally relative to the latter to form a mushroom shape. Said bulb is inserted into the tear duct sufficiently far so as to reach a shoulder located beyond the duct and thus, by abutting against the shoulder of the tear duct, forms a lock to prevent the plug escaping from the duct. These types of devices function very well. However, they are difficult to position and in particular insert into the tear duct. In order to do this it is necessary to dilate the duct to allow for the passage of the bulb of the plug.

The present invention overcomes these disadvantages by proposing a metal plug which can be positioned more easily and more rapidly into the tear duct, and, in particular, which does not require the prior dilation of the tear duct or at least only requires a slight dilation of the latter.

SUMMARY OF THE INVENTION

According to the invention such a metal plug is defined in claim 1.

The inventors have realized for the first time that by forming a bulb with an oblate and hollow shape, it is possible in a simple manner, by using a pushing-stretching device that is inserted through a hole, to prestretch the plug in the direction of the axis of the stem to reduce temporarily the thickness of the bulb and allow its insertion into the tear duct. At the same time, the fact of providing a bulb with an oblate or compacted shape makes it possible to ensure that the plug resists the operation of stretching elongation and regains a shape after the removal of the positioning device which makes it possible for it to "hold" well in the tear duct, in particular at the shoulder beyond the duct.

According to a preferred embodiment of the invention, the hole terminates in the bulb by flaring out to form a hollow chamber with a greater width dimension than the width dimension of the hole of the stem, preferably a greater width than the width dimension of the stem itself.

Preferably, at the end of the stem opposite the bulb there is a collar which projects over the stem laterally.

Preferably, the collar has a cylindrical revolution shape in relation to the axis of the stem.

Preferably, the bulb has a shape such that its outer surface is rounded without including any angular corners.

The deformation of the plug prior to its insertion into the canal is thus facilitated.

Preferably, the stem has a circular cylindrical shape.

The present invention also relates to a device for inserting a plug according to the invention.

A device according to the invention comprising a body forming a plunger device in the form of a stem, which is intended to be inserted into the hole formed in a metal plug to stretch it, is characterized in that it is provided with retaining means designed to maintain the plug in a retaining position whilst the stem is inserted therein, to stretch the plug relative to the retaining point.

According to a preferred embodiment of the invention, the retaining means are formed by two clamps arranged at the end of the device through which the stem is pushed, the at least two clamps being able to adopt a first position in which they form together an abutment in the form of a plate pierced by a hole though which the stem of plug can pass but through which a collar cannot pass, when the latter is provided at one end of the stem of the plug, and second position spaced apart from the other, in which the plug, and in particular the collar, is released from the two clamps.

Thus to insert the plug the collar is made to abut against the plate formed by the end of two clamps so as to then push the stem through the hole formed in the plug to stretch the plug and place it in the tear duct, then the stem is withdrawn and the clamps are removed to release the plug which is thus put into position.

BRIEF DESCRIPTION OF THE DRAWINGS

By way of example an embodiment of the invention is now described with reference to the drawing.

FIG. 4 is perspective view on a larger scale of an end part of the device of FIG. 3, whereas

DETAILED DESCRIPTION OF THE INVENTION

Figure 1:
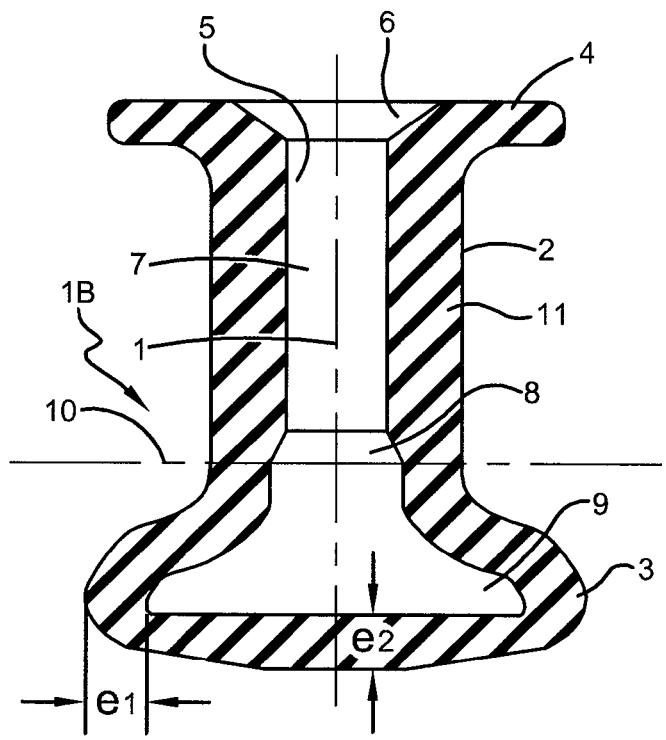
FIG. 1 shows a longitudinal cross section of a plug according to the invention.
Figure 2:
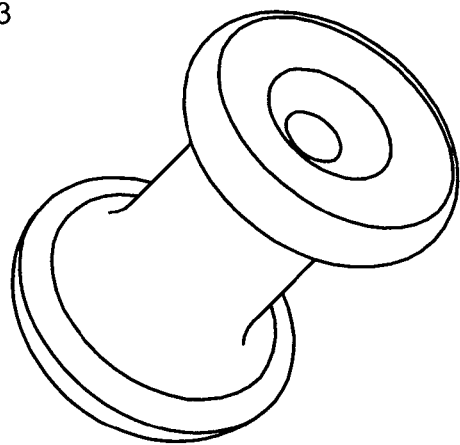
FIG. 2 shows a perspective view of a plug according to the invention.

FIG. 1 shows a longitudinal cross section of a metal plug according to the invention. This plug made from an extensible and stretchable material, in particular silicone, in particular coated with a fine layer of polyvinyl pyrrolidone, is revolutionary cylindrical in shape in relation to the longitudinal axis 1. The metal plug comprises a stem 2 of circular cylindrical shape extended at one end by a bulb 3 projecting laterally from the stem 2. At the other end of the stem 2 a collar 4 is formed, which is here substantially perpendicular to the longitudinal axis 1. According to another embodiment it is also possible to provide a collar which is inclined in relation to the longitudinal axis 1 by an angle other than 90°. A hole 5 is formed in the plug. It opens into an opening 6 from the side of the collar 4. Said hole 5 consists of a first section 7 which extends substantially over the whole length of the stem 2 to then flare out into a second intermediate section 8 and terminate in a chamber 9 on the inside of the bulb 3. The greatest width dimension (in a direction perpendicular to the axis 1) of the chamber 9 is greater than the width dimension of section 7 and also, preferably, greater than the width dimension of the stem 2.

According to the invention a parting line or plane is defined between the bulb and the stem as the line 10 which separates the stem 2 and the bulb 3. This line 10 is located at the point where the stem 2 ends, that is at the point where its outer surface starts to project beyond the substantially vertical wall 11. Below the delimitation line 10 is the stem and on the other side the bulb.

According to a preferred embodiment of the invention the hole 5 has a diameter of 0.33 mm in section 7, whereas the stem 2 has a diameter of 0.55 mm.

The greatest width dimension of the chamber 9 is approximately 0.85 mm. The great width dimension of the bulb 3 is approximately 1.1 mm. The dimension following the longitudinal axis of the bulb 3, that is the dimension between the line 10 and the tip of the bulb 3 is 0.38 mm. The length dimension of the stem 2 from the opening 6 up to the plane 10 is 1 mm. The length dimension (in the direction of axis 1) of the collar is about 0.1 mm. The greatest width dimension of the collar is about 1 mm.

The ratio of the length dimension (height) of the stem 2 to the ratio of the length dimension (height) of the bulb 3 is thus 1/0.38 or 2.6.

The ratio of the width dimension of the bulb 3 to its height dimension is 1.1/0.38, or 2.9.

The wall delimiting the cavity formed in the bulb has thickness of about 0.12 mm. The outer surface of the bulb 3 is rounded, being formed in particular in longitudinal transverse cross section (FIG. 1) by a succession of arcs of a circle. It does not contain any corners forming an angle. The thickness of the wall delimiting the section 7 of the stem 2 is 0.18 mm.

Figure 3:
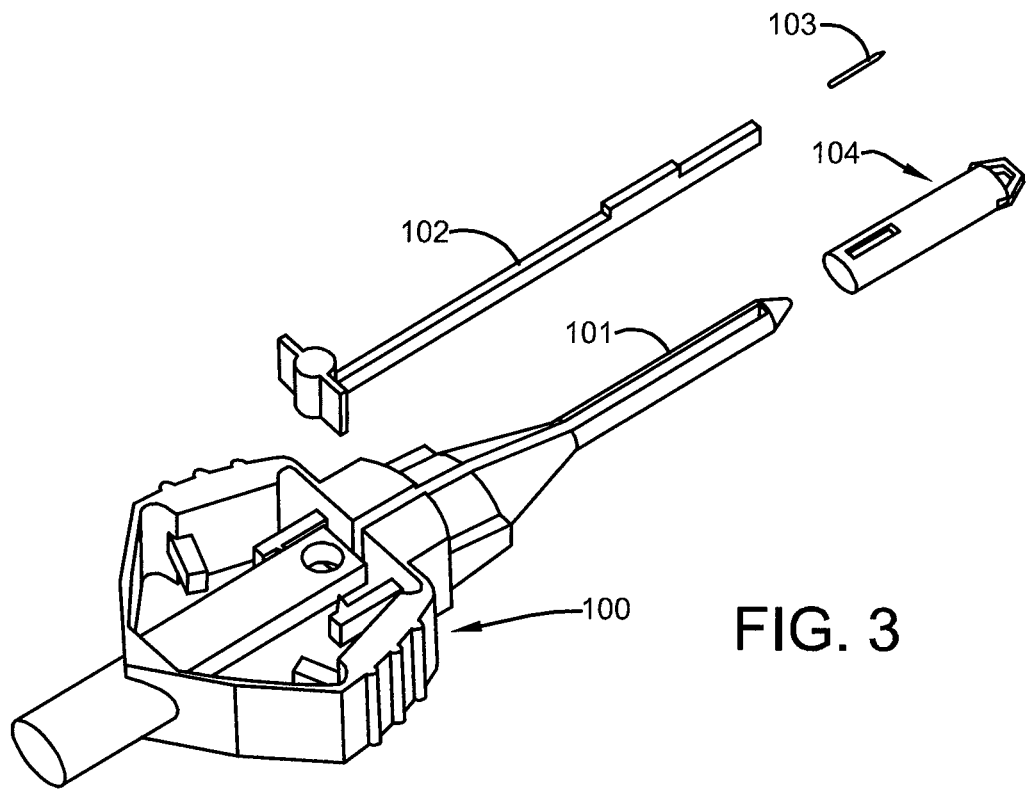
FIG. 3 is an exploded perspective view of a device for positioning and stretching according to the invention.
Figure 5:
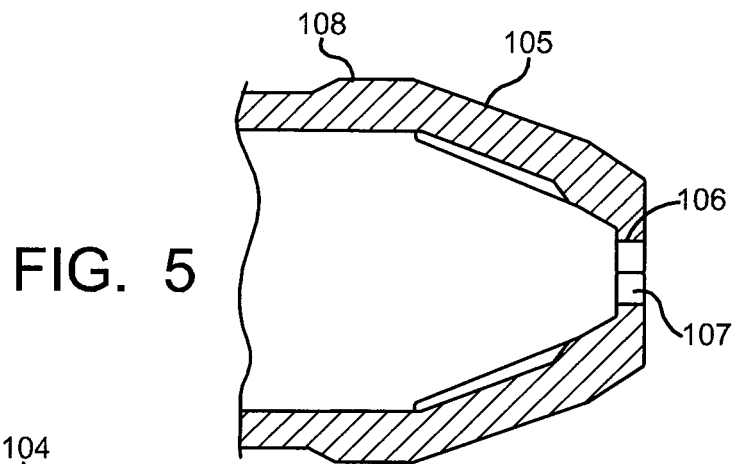
FIG. 5 is a cross section of an end part of the device of FIG. 4.
Figure 4:
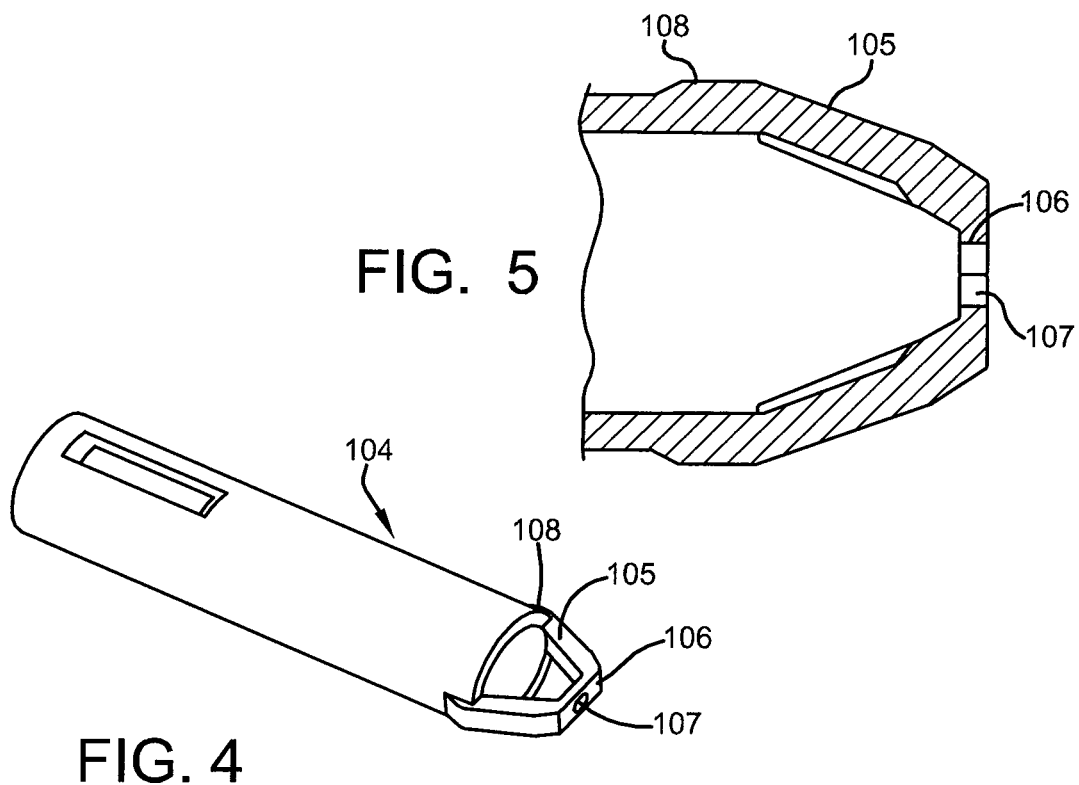

FIG. 3 shows a device intended to insert into position a plug according to the invention. This device is formed by a main body 100, in which a duct 101 is defined through which a stem 102 can be pushed. The stem 102 supports at one end a thrust needle 103 designed to be inserted into the hole 5 of the plug to just reach into the cavity 9, to push the base of the cavity 9 and stretch the wall of the bulb of the plug 9 until it is deformed, and make it less oblate to allow its insertion into the tear duct 120. At the end of the device 100, from the side where the stem 102 is going to be pushed, a sleeve 104 is provided which can be moved in relation to the body 100.

This movable sleeve 104, with a hollow circular cylindrical shape, comprises at its end, intended to be located on the side where the end 103 of the stem 102 is going to be pushed, two clamps 105, which at their free end, come into contact with one another to form an abutment plate 106, through which a hole 107 is formed, the diameter of which is such that it can grip the stem 2 without the collar 4 being able to pass through. These two clamps 105 are connected to the sleeve 104 by two thin zones 108, which thus make it possible to remove the two clamps 105 from one another in a simple manner to make it possible to release the plug.

To insert the plug into the tear duct 120, the clamps 105 are arranged so that the hole 107 encircles the stem 2, whereas the collar 4 abuts against the plate 106. Then, the stem 102 is pushed by passing it into the hollow sleeve 104 and into the hole 107 to enter into hole 5, to push and stretch the bulb 3. Once the stretched bulb 3 is made less oblate in this way, it can be pushed into the duct 120 until the bulb 3 passes the shoulder 121, which is formed at the end of the tear duct. Once in this position the stem is retracted and the clamps are removed from one another to release the metal plug.

Figure 6:
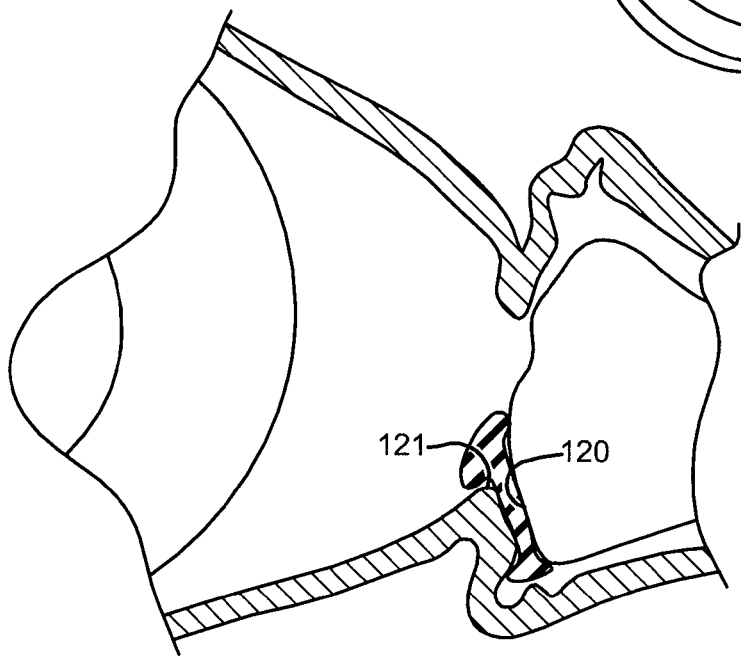
FIG. 6 is a cross section of a part of the eye of a human comprising a plug arranged according to the invention.

FIG. 6 shows a plug according to one embodiment, in which the collar is inclined at an angle other than 90° in relation to the stem, in particular from 70° to 80°, which makes it possible to a have greater conformity with the opening on the side of the tear duct of the eye.

The material used for the plug is in particular PDMS silicone or polydimethylsiloxane, in particular with a hardness level of 30 to 80 Shore, for example 50 Shore.

The material and the thicknesses of the plug, in particular the thickness or the thicknesses of the bulb, are selected so that the bulb has sufficient elasticity to regain its shape after having been pulled in the direction of the longitudinal axis of the stem and at the same time is sufficiently resistant to withstand this stretching (that is stretching such that in the stretched state the plug has a width that is almost the same as that of the stem) without being damaged.

For example for 50 Shore PDS silicone, the thickness $e_1$ of the wall of the bulb at its greatest width is preferably between 0.14 mm and 0.18 mm, in particular 0.16 mm, whereas the thickness $e_2$ of the section with the longitudinal axis is preferably between 0.10 mm and 0.20 mm, in particular 0.12 mm.

The ratio of the width of the bulb to its height is between 1 and 5, preferably between 2 and 4.

The invention claimed is:

1. Meatal plug of cylindrical shape relative to a longitudinal axis, comprising a stem and a bulb arranged at one end of the stem and protruding laterally from said stem in a transversal direction perpendicular to said longitudinal axis; said stem having a stem length along said longitudinal axis and a stem width measured in said transversal direction; said bulb having a bulb length along said longitudinal axis and a bulb greatest width measured in said transversal direction; said stem length being greater than said bulb length; said bulb greatest width being greater than said bulb length;

a cylindrical hole extending along said longitudinal axis in said stem that flares out into a hollow chamber formed in said bulb, said hole having a hole width measured in said transversal direction; said hollow chamber having a chamber length measured along said longitudinal axis and a chamber greatest width measured in said transversal direction; said chamber greatest width being greater than said hole width and said chamber greatest width being greater than said chamber length.

2. Meatal plug according to claim 1, characterised in that at the end of the stem opposite the bulb a collar is provided which projects over the stem laterally.

3. Meatal plug according to claim 1, characterised in that the bulb is shaped such that its outer surface is rounded, without any corners, the deformation of the meatal plug prior to its insertion into the canal thus being facilitated.

4. Meatal plug according to claim 1, characterised in that the meatal plug is made of silicone.

5. Meatal plug according to claim 4, wherein the plug is made of PDMS.

6. Meatal plug according to claim 1, characterised in that the meatal plug includes a wall and a thickness $e_1$ of the wall of the bulb at its greatest width is between 0.14 mm and 0.18 mm.

7. Meatal plug according to claim 6, wherein the thickness $e_1$ of the wall of the bulb at its greatest width is 0.16 mm.

8. Meatal plug according to claim 1, characterised in that the ratio of the width of the bulb to its height is between 1 and 5.

9. Meatal plug according to claim 8, wherein the ratio of the width of the bulb to its height is between 2 and 4.

10. Meatal plug according to claim 1, wherein the ratio of the width dimension of the bulb to its height is greater than 2.5.

11. Meatal plug according to claim 1, wherein the meatal plug includes a wall and a thickness $e_2$ of the wall of the bulb at the section with the longitudinal axis is between 0.10 mm and 0.20 mm.

12. Meatal plug according to claim 11, wherein the thickness $e_2$ of the wall of the bulb at the section with the longitudinal axis is 0.12 mm.

13. Meatal plug according to claim 1, wherein the width of the bulb is sufficiently large so as to allow said bulb to abut against the shoulder of a tear duct.

14. Meatal plug according to claim 13, wherein the width of the stem, measured in a direction perpendicular to the longitudinal axis, is sufficiently large so that said stem closes a tear duct.

15. Meatal plug according to claim 1, wherein said hollow chamber has its highest chamber width in the transversal direction at the end of said chamber opposite said cylindrical hole.

16. Meatal plug according to claim 1, wherein said hollow chamber is delimited by a flat bottom surface opposite said cylindrical hole.

17. Meatal plug according to claim 1, wherein in longitudinal cross-section, the outer surface of the bulb, at the beginning thereof, in continuation with the stem comprises a curved portion having its concavity turned towards the outside.

18. Meatal plug of cylindrical shape relative to a longitudinal axis, comprising a stem and a bulb arranged at one end of the stem and protruding laterally from said stem in a transversal direction perpendicular to said longitudinal axis; said stem having a stem length along said longitudinal axis and a stem width measured in said transversal direction; said bulb having a bulb length along said longitudinal axis and a bulb greatest width measured in said transversal direction; said stem length being greater than said bulb length; said bulb greatest width being greater than said bulb length;

a cylindrical hole extending along said longitudinal axis in said stem and flaring out into a hollow chamber formed in said bulb, said hole having a hole width measured in said transversal direction; said hollow chamber having a chamber length measured along said longitudinal axis and a chamber greatest width measured in said transversal direction; said chamber greatest width being greater than said hole width; said chamber greatest width being greater than said chamber length; and said bulb greatest width being measured along a line parallel to said transversal direction, which is closer to a bottom of the plug opposite the stem than to the stem.

19. Meatal plug as defined in claim 18, wherein said chamber gradually increases in width to said chamber greatest width.

20. Meatal plug as defined in claim 19, wherein said chamber greatest width is at a bottom of said chamber opposite said cylindrical hole.

\* \* \* \* \*